US00PP16084P2

(12) United States Plant Patent
Tupy et al.

(10) Patent No.: US PP16,084 P2
(45) Date of Patent: Nov. 1, 2005

(54) APPLE TREE NAMED 'UEB 3375/2'

(50) Latin Name: *Malus Mill.*
Varietal Denomination: UEB 3375/2

(75) Inventors: Jaroslav Tupy, Prague (CZ); Otto Louda, Prague (CZ); Jan Zima, Turnov (CZ)

(73) Assignee: Institute of Experimental Botany (CZ)

( * ) Notice: Subject to any disclaimer, the term of this patent is extended or adjusted under 35 U.S.C. 154(b) by 53 days.

(21) Appl. No.: 10/862,258

(22) Filed: Jun. 7, 2004

(51) Int. Cl.[7] ..... A01H 5/00
(52) U.S. Cl. ..... Plt./172
(58) Field of Search ..... Plt./172

*Primary Examiner*—Anne Marie Grunberg
(74) *Attorney, Agent, or Firm*—The Webb Law Firm

(57) ABSTRACT

A new and distinct *Malus Mill.* plant that produces apples having a pleasant aroma and harmonic sugar/acid content suitable for use as a dessert fruit.

4 Drawing Sheets

Botanical classification: *Malus Mill.*
Varietal denomination: 'UEB 3375/2'.

BACKGROUND OF THE INVENTION

The present invention comprises a new and distinct cultivar of apple tree botanically classified as *Malus Mill.* and known by the varietal name 'UEB 3375/2'. The new variety was discovered in the fall of 1999 in The Czech Republic. The new variety is the result of a planned breeding program between unpatented female parent 'Topaz' and unpatented male parent 'Golden Delicious'. The purpose of the breeding program was to find a new cultivar with high disease resistance, high yield, and excellent fruit quality. The new variety exhibits similar $V_f$—resistance against scab to 'Topaz', but there is an absence of russeting in the stem cavity. The new variety exhibits a similar tree habit, yellow ground color of fruits, and long fruit stem to 'Golden Delicious', but exhibits a globose fruit shape, the absence of fruit russeting, and the presence of $V_f$—resistance against scab. The following characteristics distinguish the new variety from other *Malus Mill.* varieties:

- Late, dessert-type, diploid variety
- Trees are of medium vigor with a spreading habit
- Fruit shape is globose with a slight ribbing
- Stalk is long and medium thick
- Russeting is absent
- Ground color of the fruit skin is yellow
- Overcolor is either absent or a very slight orange blush
- Fruit flesh is firm, juicy with a harmonic sugar/acid content, and good flavor
- Keeping quality of the fruits is very good
- $V_f$—resistance against scab is present
- Fruit of the new variety matures shortly after 'Golden Delicious'

The new variety has been trial and field tested and has been found to retain its distinctive characteristics and remain true to type through successive propagations. The new variety has not been publicly available or offered for sale anywhere in the world before the filing date of the present application. The new variety is the subject of Plant Breeders' Rights Application Number 1505/MAL08641, filed Mar. 7, 2003, in The Czech Republic, and European Community Plant Breeders' Rights Application Number 2003/1436, filed Aug. 11, 2003.

DESCRIPTION OF THE DRAWINGS

The accompanying photographic drawings illustrate the new cultivar, with the color being as nearly true as is possible with color illustrations of this type.

DESCRIPTION OF THE PLANT

Figure 1:
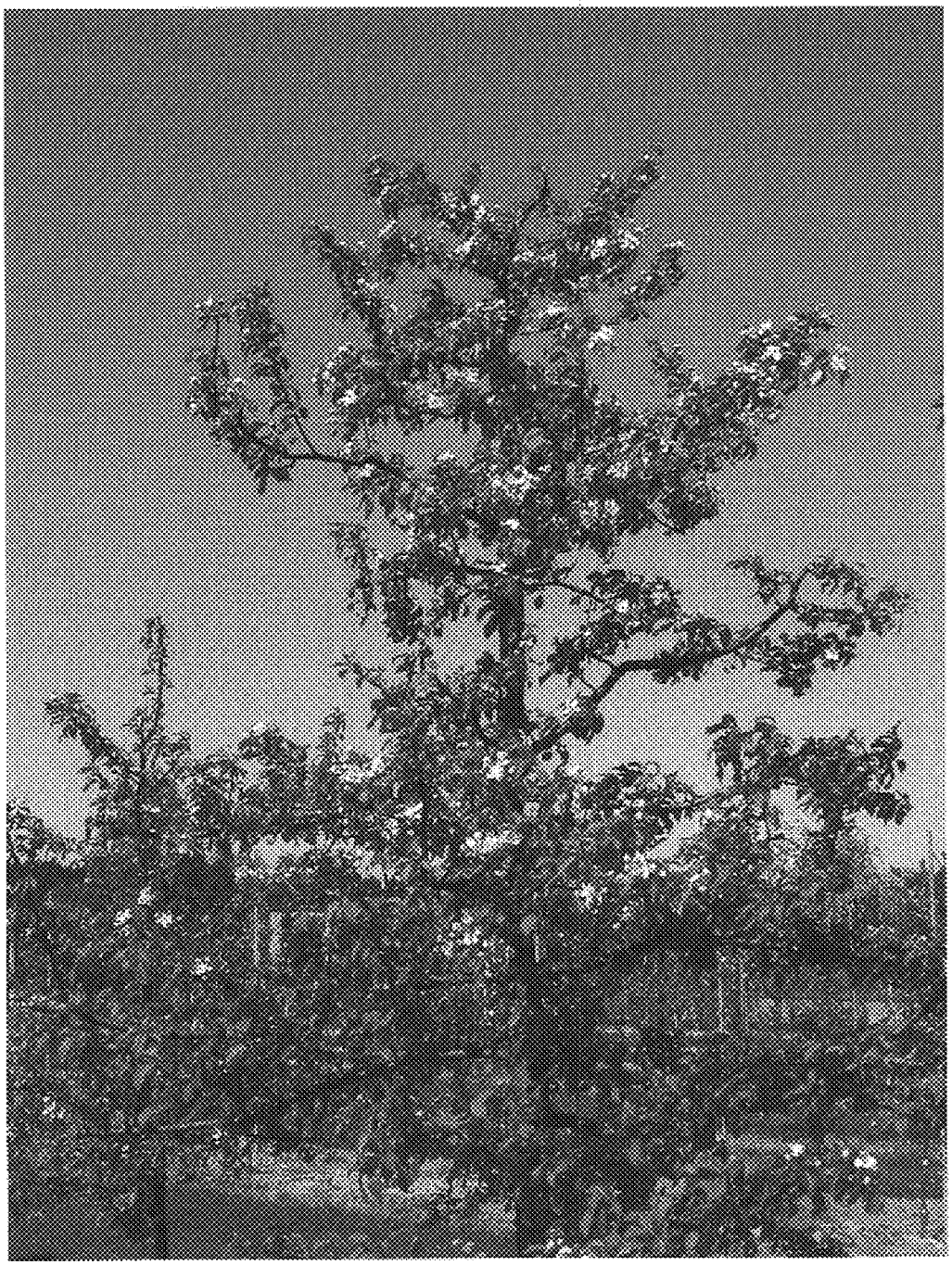
FIG. 1 shows the original seedling grown to a flowering tree.
Figure 2:
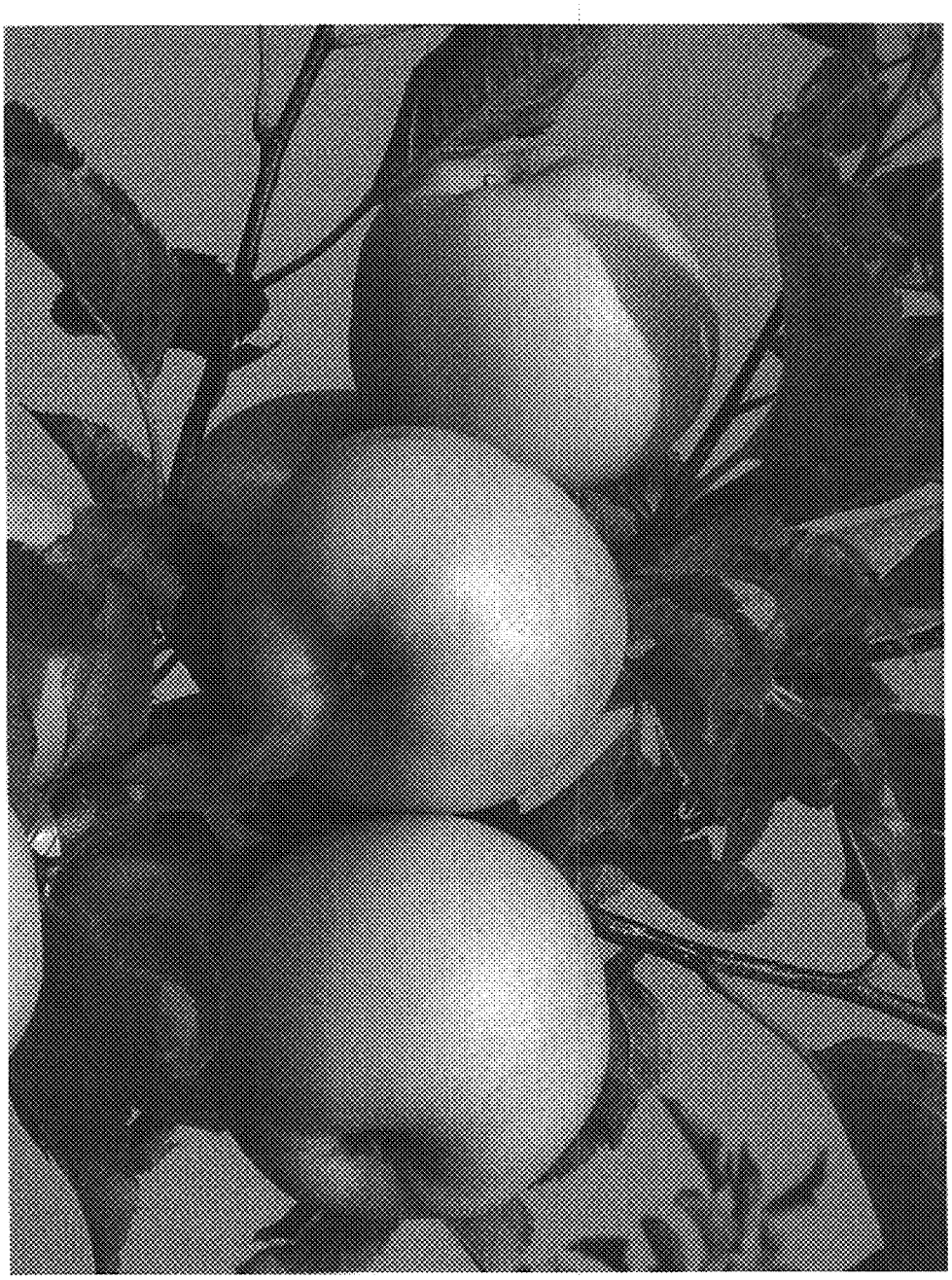
FIG. 2 shows a close-up view of the fruits of the new variety at maturity.
Figure 3:
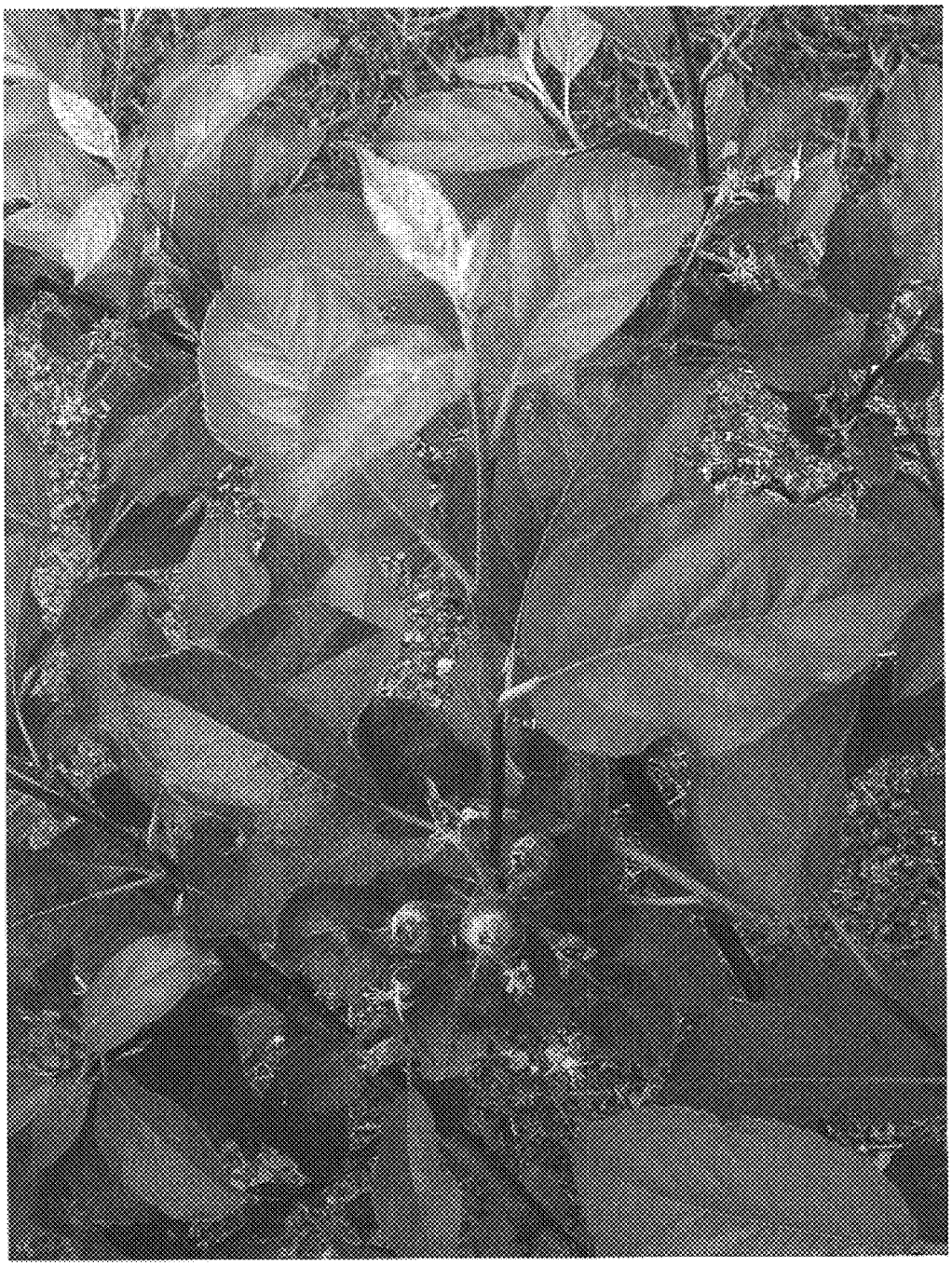
FIG. 3 shows the leaves of the new variety.
Figure 4:
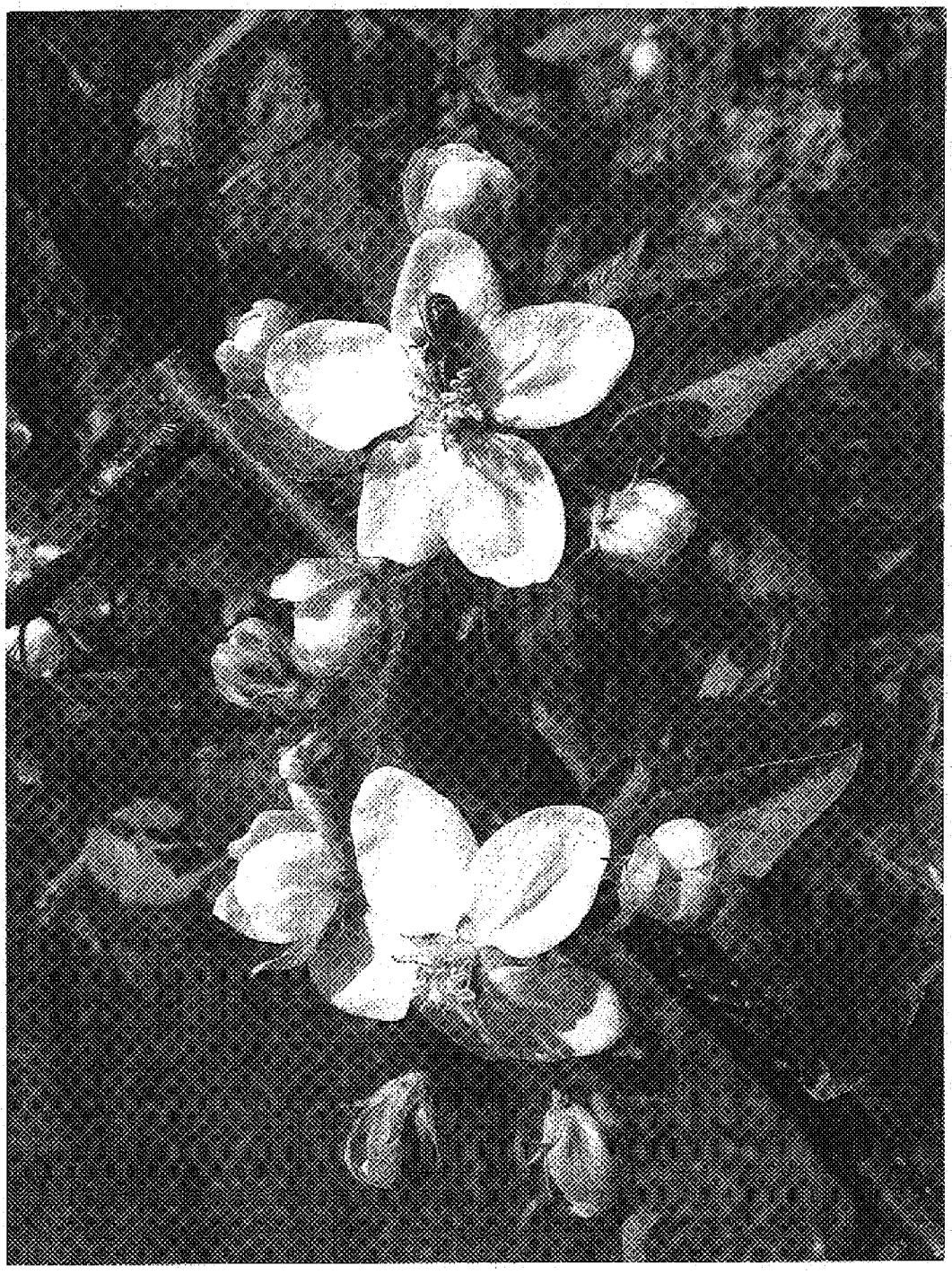
FIG. 4 shows the blossoms of the new variety.

The following detailed description sets forth the characteristics of the new cultivar. The data which defines these characteristics were collected by asexual reproductions by budding and grafting on apple tree rootstocks, including mostly 'M-9' rootstock, first carried out in The Czech Republic in the spring of 2000. The new variety was grown in a field under natural conditions with fertilization in kg/ha/year of N 55, P 25, K 60, Ca 55, and Mg 5. The color readings were taken in natural daylight. Color references are primarily to The R.H.S. Colour Chart of The Royal Horticultural Society of London.

TREE

Age: 9 years old.
Size: At crown — 2.6 m high, 2.8 m wide.
Vigor: Medium.
Density: Medium.
Form: Spreading.
Production: Very early, high and regular.
Growth type: Ramified.
Bearing: Annual bearing on spurs and one-year-old shoots.
Trunk:
*Size.*—Height 100.0 cm, diameter at soil 15.0 cm.
*Surface texture.*—Semirough.
*Bark color.*—Greyed-orange RHS 172C.

*Lenticels.*—Length: 2.0 mm, often associated in up to 3.0 cm bands. Width: 1.0 to 2.0 mm. Color: Grey-brown RHS 199D. Density: Medium.

Branches:

*Diameter.*—Lower branches at the trunk are 5 cm.

*Surface texture.*—Smooth.

*Color.*—Greyed-purple RHS 183A.

*Form.*—Ramified.

*Average angle.*—80°.

*Bud arrangement.*—Typically small pointed flower buds on short spurs and one-year-old shoots.

*Lenticels.*—Length: 1.0 to 2.0 mm. Width: 1.0 to 2.0 mm. Shape: Round to oval. Density: Medium. Color: Grey-grown RHS 199D.

Leaves:

*Length.*—95.0 mm.

*Width.*—56.0 mm.

*Form.*—Oval to lanceolate.

*Texture.*—Smooth, glossy.

*Thickness.*—Medium.

*Base.*—Regular.

*Apex.*—Acuminate.

*Margin.*—Sharp, serrated.

*Pubescence.*—Upper surface: Weak to absent. Lower surface: Weak.

*Color.*—Young leaves: Upper surface: Yellow-green RHS 146A–B. Lower surface: Yellow-green RHS 147C. Mature leaves: Upper surface: Yellow-green RHS 147A to Green 137A. Lower surface: Green RHS 138B.

*Petiole.*—Shape: Mostly straight. Length: 29.0 mm. Diameter: 1.8 mm. Color: Yellow-green RHS 147B, lower surface purplish to purple.

*Veins.*—Venation type: Medium dense with a 45° angle between the main veins. Color: Upper surface: Yellow-green RHS 147B. Lower surface: Yellow-green RHS 145C.

Flower buds:

*Pedicel.*—Length: 29.0 mm. Diameter: 1.0 mm. Color: Yellow-green RHS 144B.

*Bud.*—Length: 17.0 mm. Width: 15.0 mm. Color: Red-purple RHS 67D of various intensity.

Flowers:

*Bloom timing.*—Medium to late May 5, but varies depending on location and year; 1–2 days before 'Golden Delicious'.

*Blooming period.*—Medium to long.

Pollination requirements: Normal, good pollinators, similar to crab apple 'Golden Hornet'.

*Number of flowers per cluster.*—5 to 6.

*Fragrance.*—Medium.

*Petals.*—Number: 5. Length: 23.0 mm. Width: 16.0 mm. Shape: Ovate. Aspect: Position overlapping. Margin: Straight. Texture and appearance: Venation is purplish, surface is waved. Color: When opening: Upper surface: Purple RHS 76D and purple RHS 77D. Lower surface: Purple RHS 76D and red-purple RHS 70C. Fully opened: Upper surface: White RHS 155C and purple RHS 76C–D. Lower surface: Purple RHS 76D, with sections of purple RHS 77D.

*Sepals.*—Shape: Acuminate. Margin: Straight. Length: 8.0 mm. Width: 4.0 mm. Color: Upper surface: Yellow-green RHS 144B. Lower surface: Yellow-green RHS 145B, at tip purplish.

*Stamens.*—Number (per flower): 20. Filament length: 5.0 to 11.0 mm.

*Anthers.*—Shape: Irregular. Length: 2.0 mm. Color: Yellow RHS 10C.

*Pollen.*—Color: Yellow RHS 10B. Amount (generally): High.

*Pistils.*—Length: 17.0 mm.

*Style.*—Length: 13.0 mm. Color: Yellow-green RHS 145A.

*Stigma.*—Shape: Round. Color: Yellow-green RHS 150B.

Fruit:

*Maturity when described.*—Three months after picking.

*Date of picking.*—Oct. 8, 2003.

*Size.*—Axial diameter: 67.0 mm. Transverse diameter: 74.0 mm.

*Form.*—Globose.

*Cavity.*—Shape: Funnel-shaped. Depth: Medium, 15.0–18.0 mm. Breadth: Medium, 38.0 mm.

*Basin.*—Shape: Funnel-shaped with small numerous ribbings. Depth: Medium, 5.0–6.0 mm. Width: Medium, 35.0 mm.

*Calyx.*—Persistent, open, green.

Skin:

*Thickness.*—Medium to thin.

*Texture.*—Smooth, without russeting.

*Tendency to crack.*—No.

*Color.*—Yellow, occasionally with slight orange blush RHS 25B.

*Ground color.*—Mostly yellow RHS 13B.

Flesh:

*Aroma.*—Good distinctive flavor, harmonic sugar/acid content.

*Color.*—Yellow-orange RHS 16D.

*Texture.*—Fine.

*Eating quality.*—Very good.

Core:

*Bundle area.*—Core with seed cells round on longitudinal section, 20 mm diameter.

*Bundle.*—Strands of conductive tissue on longitudinal section onion shaped, height of 30.0 mm, width of 35.0 mm.

*Capillary area.*—Eye basin medium deep and wide, height of 30.0 mm, width of 35.0 mm, ribbed.

*Calyx tube.*—Medium long, open, narrow funnel shaped.

*Depth of tube to shoulder.*—16.0 mm.

*Styles.*—Present as dry residues.

*Stamens.*—Present as dry residues.

*Axillary cavity.*—Stalk cavity medium, depth of 5.0–6.0 mm, width of 35.0 mm.

*Seed cells.*—Wall: Medium thick. Depth: 10.0 mm. Breadth: 3.0–5.0 mm. Longitudinal section: Length of 18–20 mm.

Seeds:

*Number perfect.*—7–9.

*Number in one cell.*—1–2.

*Length.*—9.0 mm.

*Breadth.*—5.0 mm.

*Form.*—Usual apple seed form.

*Color.*—Greyed-orange RHS 175A–B.

Stem:

*Length.*—19.0 to 24.0 mm.

*Width.*—1.5 to 2.0 mm.

*Color.*—Yellow-green, closest to RHS 153B.

Use: Late, dessert variety for conventional and ecological fruit growing.

Shipping quality: Very good.

Keeping quality: Very good. Six months under natural storage, in comparison to only four months for 'Golden Delicious'.

Tree winter hardiness: No frost damage observed so far at the place of origin.

Bud winter hardiness: No frost damage observed so far at the place of origin.

Drought tolerance: Unknown.

Disease resistance: $V_f$- resistance against scab, tolerant to powdery mildew, no other diseases observed so far on trees untreated with fungicides.

I claim:

1. A new and distinct variety of *Malus Mill*. plant, substantially as shown and described.

* * * * *